(12) United States Patent
Itoh

(10) Patent No.: US 12,013,334 B2
(45) Date of Patent: Jun. 18, 2024

(54) SPECIMEN INFORMATION DETECTION APPARATUS AND SPECIMEN INFORMATION DETECTION METHOD

(71) Applicant: Aoi Seiki Co., Ltd., Kumamoto (JP)

(72) Inventor: Teruaki Itoh, Kumamoto (JP)

(73) Assignee: Aoi Seiki Co., Ltd., Kumamoto (JP)

( * ) Notice: Subject to any disclaimer, the term of this patent is extended or adjusted under 35 U.S.C. 154(b) by 373 days.

(21) Appl. No.: 17/369,702

(22) Filed: Jul. 7, 2021

(65) Prior Publication Data

US 2022/0011294 A1 Jan. 13, 2022

(30) Foreign Application Priority Data

Jul. 10, 2020 (JP) .................................. 2020-119101

(51) Int. Cl.
| | |
|---|---|
| *G01N 33/49* | (2006.01) |
| *G01N 21/25* | (2006.01) |
| *G01N 33/487* | (2006.01) |
| *G01N 33/72* | (2006.01) |
| *G06T 7/00* | (2017.01) |
| *G06T 7/90* | (2017.01) |

(Continued)

(52) U.S. Cl.
CPC ....... *G01N 21/251* (2013.01); *G01N 33/4875* (2013.01); *G01N 33/49* (2013.01); *G01N 33/72* (2013.01); *G06T 7/0012* (2013.01); *G06T 7/90* (2017.01); *G06V 10/44* (2022.01); *G06V 10/56* (2022.01); *G06V 30/2247* (2022.01)

(58) Field of Classification Search
CPC .. G01N 21/251; G01N 33/4875; G01N 33/49; G01N 33/72; G06T 7/90; G06T 7/0012; G06V 10/56; G06V 30/2247; G06V 10/44
See application file for complete search history.

(56) References Cited

U.S. PATENT DOCUMENTS

| | | |
|---|---|---|
| 7,771,659 B2 | 8/2010 | Ziegler |
| 2005/0163354 A1 | 7/2005 | Ziegler |

(Continued)

FOREIGN PATENT DOCUMENTS

| | | |
|---|---|---|
| JP | 2001165752 A | 6/2001 |
| JP | 2008-076185 | 4/2008 |

(Continued)

OTHER PUBLICATIONS

Extended European Search Report in Application No. 21183743.0, dated Nov. 22, 2021, 13 pages.

(Continued)

*Primary Examiner* — Jamil Ahmed
(74) *Attorney, Agent, or Firm* — Knobbe, Martens, Olson & Bear, LLP

(57) ABSTRACT

According to an aspect of the invention, a specimen information detection apparatus includes, an image capture device configured to capture an image of a specimen container that contains a specimen, an illumination device configured to irradiate the specimen container with light sideways with respect to an image capturing direction when the image is captured, and an information processing portion configured to detect a state in the specimen container through image processing based on image information of the specimen container acquired by capturing the image of the specimen container.

7 Claims, 8 Drawing Sheets

(51) Int. Cl.
  *G06V 10/44*    (2022.01)
  *G06V 10/56*    (2022.01)
  *G06V 30/224*   (2022.01)

(56) References Cited

U.S. PATENT DOCUMENTS

| | | | |
|---|---|---|---|
| 2006/0014295 A1* | 1/2006 | Ziegler | G01N 35/0092 |
| | | | 436/164 |
| 2007/0134131 A1* | 6/2007 | Watson | B65G 47/1471 |
| | | | 422/65 |
| 2008/0069730 A1 | 3/2008 | Itoh | |
| 2010/0303331 A1* | 12/2010 | Itoh | G01N 21/251 |
| | | | 382/134 |
| 2013/0076882 A1* | 3/2013 | Itoh | G01N 21/25 |
| | | | 382/134 |
| 2018/0059006 A1 | 3/2018 | Fritchie et al. | |

FOREIGN PATENT DOCUMENTS

| | | |
|---|---|---|
| JP | 2012047589 A | 3/2012 |
| TW | 201109663 | 3/2011 |
| WO | WO 2017/132167 A1 | 8/2017 |

OTHER PUBLICATIONS

Office Action in TW110124422, dated May 3, 2022.
Office Action received in Japanese Application No. 2020-119101, dated Dec. 19, 2023.

* cited by examiner

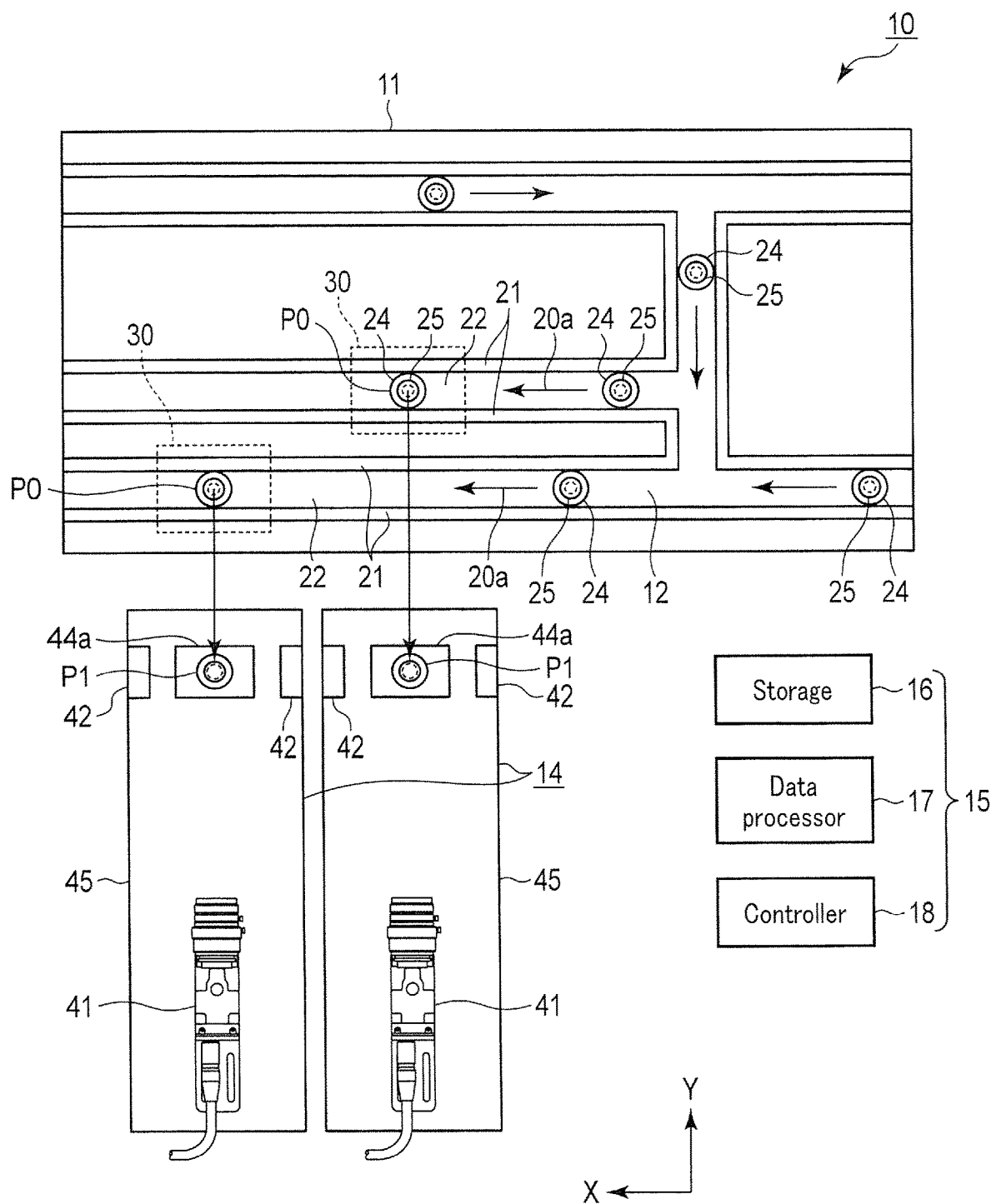
F I G. 1

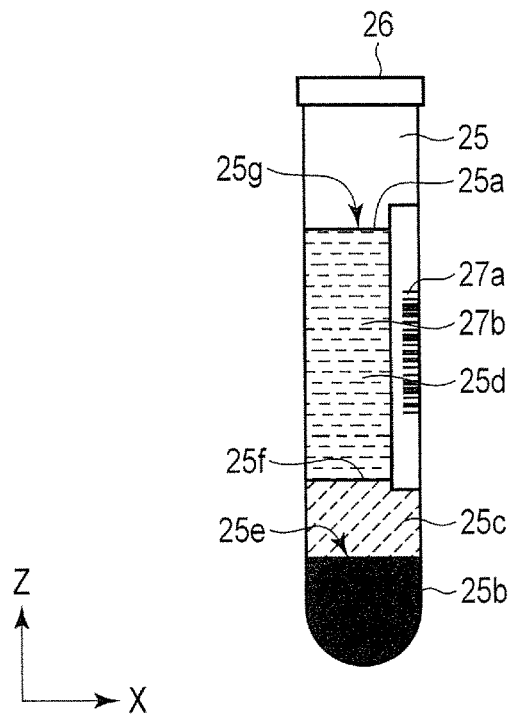
F I G. 3
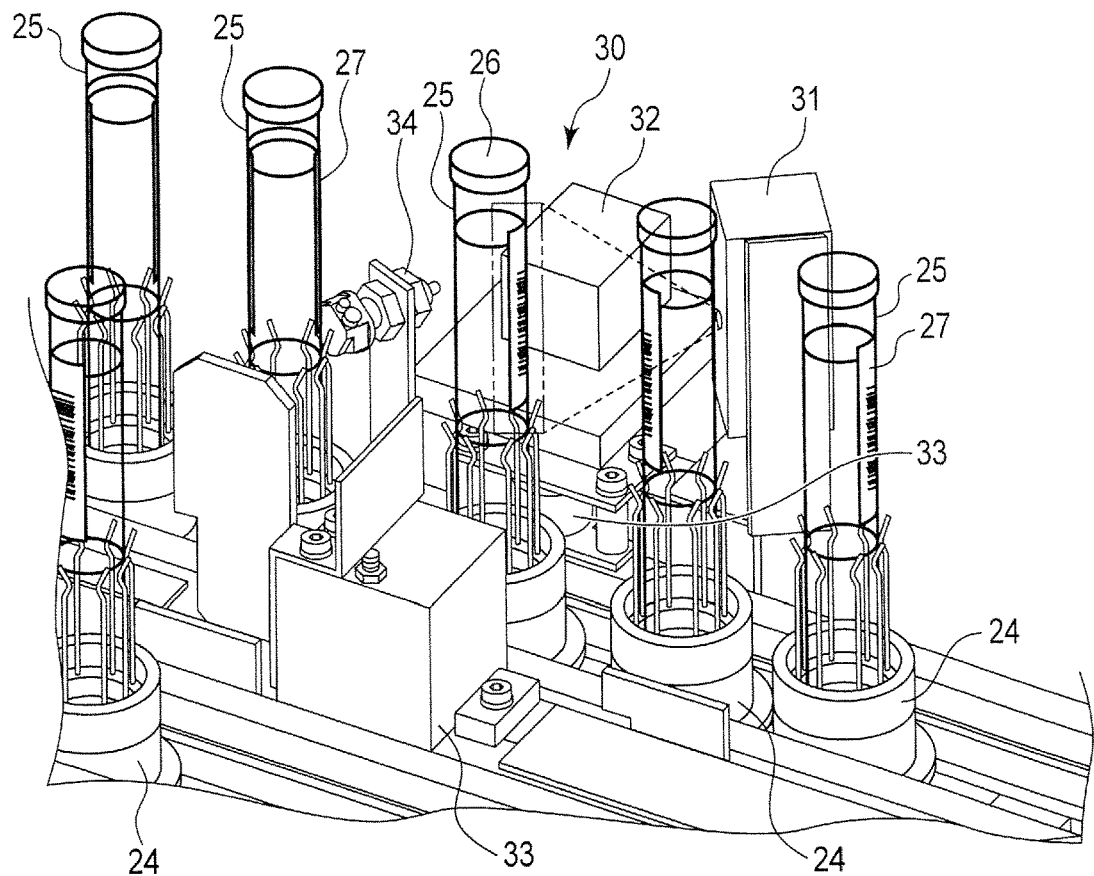
F I G. 4

SPECIMEN INFORMATION DETECTION APPARATUS AND SPECIMEN INFORMATION DETECTION METHOD

CROSS-REFERENCE TO RELATED APPLICATION

This application is based upon and claims the benefit of priority from the prior Japanese Patent Application No. 2020-119101, filed Jul. 10, 2020 the entire contents of which are incorporated herein by reference.

FIELD

The present invention relates generally to a specimen information detection apparatus and a specimen information detection method.

BACKGROUND

As preprocessing of processing for various kinds of blood tests such as biochemical analyses, for example, an image of a specimen container is acquired and a condition of a specimen before a test is detected based on the image. For example, the specimen container is made of transparent material, such as glass (Jpn. Pat. Appln. KOKAI Publication No. 2008-76185).

In specimen containers in general, a label indicating information on the specimen, such as identification information, is attached to an outer circumferential surface. In this case, it is difficult to detect a condition of the specimen in the container from the image of an appearance of the specimen container.

In the preprocessing before a test as described above, it is required to detect a condition of the specimen with a high accuracy at a high efficiency.

SUMMARY

According to an aspect of the invention, a specimen information detection apparatus comprises, an image capture device configured to capture an image of a specimen container that contains a specimen, an illumination device configured to irradiate the specimen container with light sideways with respect to an image capturing direction when the image is captured, and an information processing portion configured to detect a state in the specimen container through image processing based on image information of the specimen container acquired by capturing the image of the specimen container.

According to another aspect of the invention, the illumination device is configured to irradiate the specimen container with light emitted from both sides in a light irradiation direction intersecting the image capturing direction in which the specimen container aligns with an image detection axis when the image is captured, the specimen information detection apparatus further comprising:

a chamber configured to house the specimen container and block an external light when the image is captured; and a position adjustment device configured to adjust an orientation of a label attached to an outer circumferential surface of the specimen container before the image is captured.

According to another aspect of the invention, the information processing portion is configured to:

detect contrasting density information of an image in a target region through image processing from image information of the specimen container acquired by capturing an image of the specimen container prior to a test process of the specimen to detect a chylous state of the specimen based on the contrasting density information; and detect color information of the specimen through image processing from the image information to detect a hemolysis state of the specimen based on the color information.

According to another aspect of the invention, the information processing portion is configured to detect a contrast in a target region from the image information through image processing to detect a foreign-substance containing state of the specimen based on the contrast.

According to another aspect of the invention, a specimen information detection method comprises:

capturing an image of a specimen container that contains a specimen;

irradiating the specimen container with light sideways with respect to an image capturing direction when the image is captured; and detecting a state in the specimen container through image processing based on image information of the specimen container acquired by capturing the image of the specimen container.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

FIG. 1 is a plan view showing a configuration of a specimen information detection apparatus according to a first embodiment of the present invention.

FIG. 3 is an explanatory view showing a test tube and a specimen according to the embodiment.

FIG. 4 is a perspective view showing apart of the specimen information detection apparatus according to the embodiment.

DETAILED DESCRIPTION

First Embodiment

Figure 2:
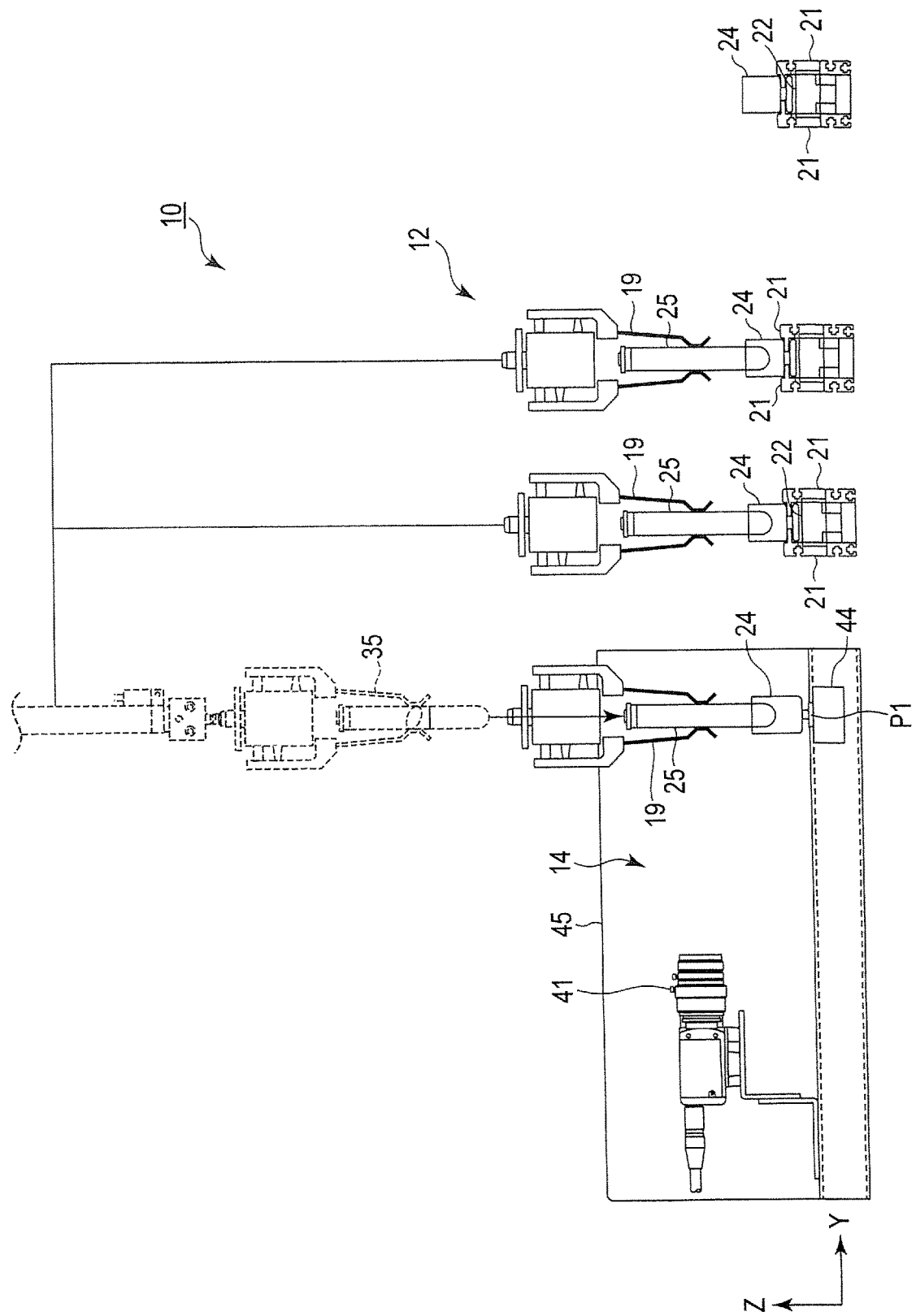
FIG. 2 is a side view showing a configuration of the specimen information detection apparatus.

Hereinafter, a specimen information detection apparatus 10 and a specimen information detection method according to an embodiment of the present application will be described with reference to FIG. 1 to FIG. 8. In the drawings, components are enlarged, reduced, or omitted as needed. Arrows X, Y, and Z in the drawings respectively indicate three directions perpendicular to one another.

FIG. 1 and FIG. 2 are explanatory views schematically showing the specimen information detection apparatus 10 according to the embodiment. FIG. 3 is an explanatory view showing a test tube, which is a specimen container, and a specimen contained therein. The specimen information detection apparatus 10 is a preprocessing apparatus which detects a condition of a specimen in advance before various kinds of test processing such as a biochemical analysis of the specimen, and is used as a preprocessing apparatus of, for example, an analysis apparatus. In this embodiment, as test inhibiting factors, foreign substances containing states such as the presence of a fibrin and defective blood clotting are detected as well as a chyle and hemolysis.

The specimen information detection apparatus 10 includes an apparatus main body 11, a conveyance portion 12 that conveys a test tube 25 (specimen container) along a predetermined conveyance pathway 20a (conveyance path), an image acquisition portion 14 that acquires image information by capturing an image of the specimen, and a test inhibiting factor detection portion 15 that performs test inhibiting factor detection processes based on various kinds of images acquired by the image acquisition portion 14.

As shown in FIGS. 1 and 2, the conveyance portion 12 is a conveyor type holder conveyance mechanism provided above the apparatus main body 11. The conveyance portion 12 includes a pair of guide rails 21 disposed in a predetermined width along the conveyance pathway 20a extending in the X axis direction in the drawings, a conveyor belt 22 arranged between the guide rails 21 along the conveyance pathway 20a, and a driving portion such as a conveyance roller that rotationally drives the conveyor belt 22 from the lower side to feed it. The specimen information detection apparatus 10 also includes a read unit 30 disposed at a pickup position P0 of the conveyance pathway 20a, and a transfer device 19 that transfers the test tube 25 between the pickup point (pickup position) P0 and an image capturing point P1 (image capturing position) on the conveyance pathway 20a.

The read unit 30 includes a bar-code reader 31 that detects information on a label 27 attached to the test tube 25, a label sensor 32 that detects a position of a label 27, a rotation device 33 that serves as a position adjustment device and that rotates the test tube 25, and a position sensor 34 that detects a presence or absence of the test tube 25.

The bar-code reader 31 reads, for example, identification information indicated on the label 27 of the test tube 25 on the conveyance pathway 20a.

The label sensor 32 detects a position of an edge 27d of the label 27 of the test tube 25, thereby detecting an orientation of the test tube 25.

The rotation device 33 rotates the test tube 25 on the conveyance pathway 20a, thereby moving an outer circumferential surface of the test tube 25 during a label reading process. The rotation device 33 adjusts the amount of rotation, thereby adjusting the orientation of the test tube 25 to be suitable for image capturing in the next step.

For example, the rotation device 33 includes a roller that rotates in a state of being in contact with an external surface of the test tube 25 or an external surface of a holder 24, and rotates the test tube 25 by the rotation of the roller. The rotation device 33 is controlled by a controller 18, and rotates at a predetermined timing and by a predetermined amount of rotation, thereby rotating the test tube 25 and adjusting the position of the test tube 25 suitable to the image capturing direction, so that the overall circumferential surface of the test tube 25 can be sequentially read during the read process by the read unit 30.

The transfer device 19 includes a robot arm. The transfer device 19 transfers the test tube 25 on the conveyance pathway 20a to an image capturing point P1 in a chamber 45 of the image acquisition portion 14, while maintaining the test tube 25 in an upright state, or takes the test tube 25 out from the chamber 45 after the image capturing and returns it to the conveyance pathway 20a.

The test tube 25 as a specimen container containing a specimen 25a is held by the holder 24 and conveyed along the conveyance pathway 20a in the upright state. The holder 24 engages between the pair of guide rails 21, and is conveyed as the conveyor belt 22 moves. By means of various processing devices disposed along the conveyance pathway 20a, the test tube 25 or the specimen 25a undergoes various processing. The test tube 25 is transferred by the transfer device 19 from the conveyance pathway 20a to the image capturing point P1 in the chamber 45 while being maintained in the upright state, and undergoes an image capturing process (photographing process). The test tube 25 that has undergone the image capturing process is returned to the conveyance pathway 20a by the transfer device 19 again and fed to the downstream side.

As shown in FIG. 3, the test tube 25 is made of transparent glass or the like, so that the specimen inside can be visually observed from outside. The test tube 25 has a bottomed cylindrical shape having a cylindrical space to store the specimen. For example, the label 27 is attached to an outer circumferential side surface of the test tube 25 by a bond or adhesive.

The label 27 includes a print portion 27a indicating a bar code or the like that represents various kinds of information, such as identification information of the specimen 25a. The label 27 is attached to a part of an outer circumference of the test tube 25, and covers a predetermined area of the circumferential surface of the test tube 25. A pair of edges 27d, namely both ends in the circumferential direction of the label 27, are separated from each other; in other words, the test tube 25 includes an exposed portion 27b in at least a part of the outer circumferential surface where no label 27 is attached. In the exposed portion 27b, the specimen inside the transparent test tube 25 can be visually observed from outside.

The specimen 25a in the test tube 25 is separated into a blood clot layer 25b, a separating medium (silicone) layer 25c, and a blood serum layer 25d, the three layers being arranged sequentially from the lower side in the order named. A first interface 25e is formed between the blood clot layer 25b and the separating medium layer 25c. A second interface 25f is formed between the separating medium layer 25c and the blood serum layer 25d. A specimen liquid surface 25g, which is a third interface, is formed on the blood serum layer 25d.

An area of the blood serum layer 25d of a predetermined width is exposed through a side periphery of the test tube 25. In this embodiment, an example is described in which the test tube 25 includes the exposed portion 27b formed in advance in a part of the test tube 25 where the label 27 is not attached. However, the exposed portion 27b may be formed by peeling off a predetermined area of the label 27 in advance by another preprocessing.

As shown in FIG. 1 and FIG. 2, the image acquisition portion 14 includes an image capture portion 41 (image detection means) serving as an image capture device that captures a side of the test tube 25 to acquire image information of the specimen, sidelights 42 serving as illumination devices that irradiate the test tube 25 with light sideways with respect to an image capturing direction, and the chamber 45 that accommodates these components.

The sidelights 42 are comprised of a pair of white LEDs disposed on both sides of the test tube 25 assuming that the image capture portion 41 is located on a front side, and irradiates the test tube 25 sideways in directions intersecting an image detection axis, which coincides with an image capturing direction for the test tube 25. As an example, in this embodiment, the image detection axis is along a Y direction and the irradiation direction is along an X direction, and the X and Y directions are perpendicular to each other. The sidelights 42 are comprised of, for example, white LEDs and irradiate the test tube 25 with light sideways. At the image capturing point P1, the test tube 25 is set such that the exposed portion 27b is located on the image capture front surface.

The image capture portion 41 (image detection means) is, for example, a CCD camera including an image sensor, and is provided on a side of the image capturing point P1 on the conveyance pathway. The image capture portion 41 captures an image of the circumferential surface of the test tube 25 maintained in the upright state at the image capturing point P1 from a side of the conveyance pathway, and acquires image information. The acquired image information is recorded in a storage 16, and sent to a data processor 17.

The chamber 45 is disposed on, for example, a side of the conveyance pathway 20a. The image capturing point P1 is provided at a predetermined position of an inner bottom portion of the chamber 45, and the holder 24 is placed at the position. An upper surface of the chamber 45 is provided with a lid that can be opened and closed when the test tube 25 is put into and taken out from the chamber 45.

The image acquisition portion 14 operates under the control of the controller 18, and performs sidelight image capturing to capture an image irradiated with light emitted from both sides in directions different from the image capturing direction at a predetermined timing.

At the time of sidelight image capturing, the image capture portion 41 irradiates the test tube 25 with light emitted sideways and captures the image from the front side, thereby acquiring the image information of the specimen 25a in the transparent test tube 25. At this time, the optical axis of the image capture portion 41 is along the Y direction, while the optical axis of illumination light is along the X direction. Thus, the optical axis of the image capture portion 41 and the optical axis of the illumination light are different in direction. For example, the optical axis of the image capture portion 41 and the optical axis of the illumination light form an angle of 60 degrees or greater and 90 degrees or smaller.

The image capture portion 41 and the sidelights 42 are set to a positional relationship in which, for example, the light emitted from the sidelights 42 enters the test tube 25 through the exposed portion 27b and the incident light reflects at the inner wall of the test tube 25, and thereby the light is input to the image capture portion 41 without transmitting through the print portion 27a of the label 27. As an example, the sidelights 42 are disposed so that a center angle between the direction of light and the image capturing direction at a center position of the test tube 25 is in a range of 45 degrees or greater and 90 degrees or smaller. Preferably, the sidelights 42 are disposed so that a center angle between the direction of light and the image capturing direction at a center position of the test tube 25 is in a range of 60 degrees or greater and 90 degrees or smaller. In such a positional relationship, the light emitted from the sidelights 42 enters the test tube 25 through the exposed portion 27b and the incident light is reflected and refracted at the rear surface of the label 27 attached to the circumferential surface of the test tube 25 as a light reflector, so that light not passed through the print portion 27a on the front surface of the label 27 can be detected and an image thereof can be captured.

The test inhibiting factor detection portion 15 includes the image acquisition portion 14 as well as the storage 16 (storage means) that stores various data including image information, the data processor 17 (information processing portion) that performs data processing, such as calculation and determination including image processing, based on the various data, and the controller 18 (control means) that controls operations of the respective components.

Figure 5:
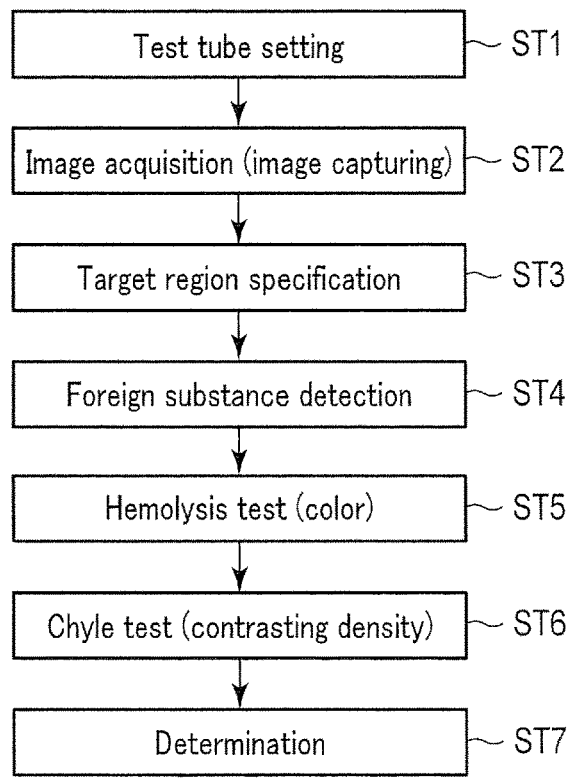
FIG. 5 is an explanatory view showing a processing procedure of a specimen processing method according to the embodiment.
Figure 6:
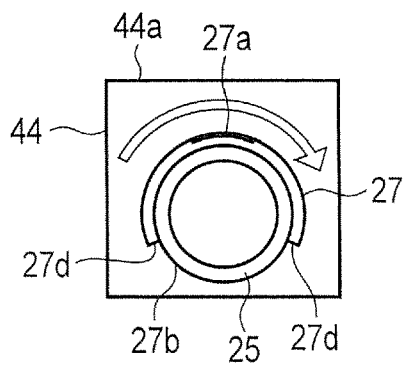
FIG. 6 is an explanatory view showing a positional relationship in an image capturing process in the specimen information detection method.
Figure 6:
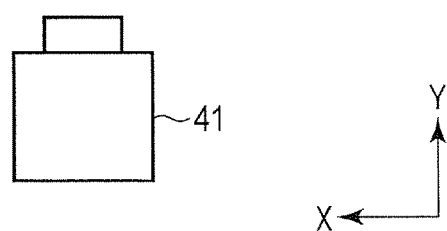
Figure 7:
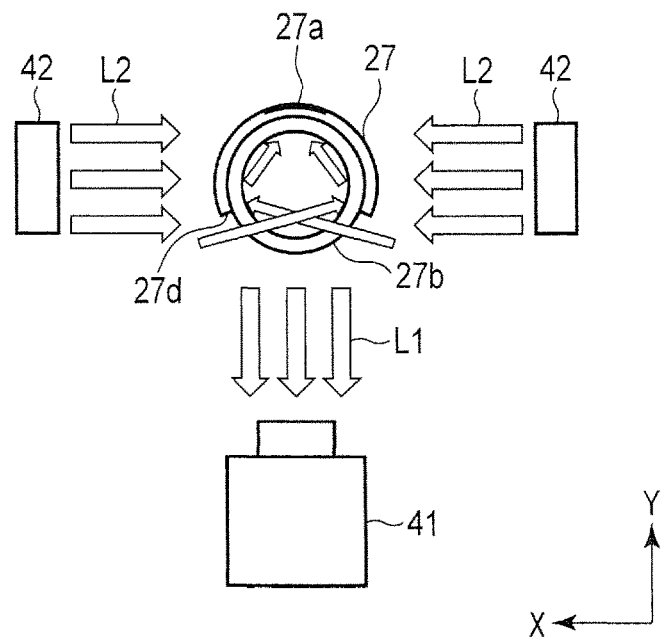
FIG. 7 is an explanatory view showing a positional relationship in an image capturing process in the specimen information detection method.

A specimen information detection method according to the present invention will be explained with reference to FIG. 4 and the flowchart of FIG. 5. FIG. 4 is a perspective view showing a part of the specimen information detection apparatus. FIG. 5 is an explanatory view showing a processing procedure of a specimen processing method. FIG. 6 and FIG. 7 are explanatory views showing a positional relationship in an image capturing process.

In step ST1, the controller 18 causes the transfer device 19 to hold the test tube 25 conveyed through the conveyance pathway 20a at the pickup point P0, and sets the test tube 25 at the image capturing point P1 in the chamber 45. As preprocessing before the setting step, the controller 18 causes the bar-code reader 31 to perform a read process for reading identification information of the label 27, the label sensor 32 to detect an edge position, and the rotation device 33 to perform a rotation process for rotating the test tube 25. For example, when the bar-code reader 31 performs reading, the controller 18 causes the label sensor 32 to detect a position of the edge 27d of the label 27 of the test tube 25 on the conveyance pathway 20a, and adjusts the rotation amount of the rotation device 33 based on information on the detected position of the edge 27d, thereby adjusting the orientation of the test tube 25.

At this time, the test tube 25 is set to an orientation so that the light emitted from the sidelights 42 can enter the test tube 25 through the exposed portion 27b in a subsequent image capturing step, and so that the incident light can reflect at the inner wall of the test tube 25 and can be input to the image capture portion 41 without transmitting through the print portion 27a of the label 27. As an example, the controller 18 sets the test tube 25 in such a position that the exposed portion 27b faces the camera and the print portion 27a of the label 27 faces an opposite side of the camera as viewed in the image capturing direction. Then, the transfer device 19 transfers the test tube 25, so that the test tube 25 is placed at the image capturing position of the chamber 45 in an orientation in which the exposed portion 27b faces the camera. The lid is opened or closed at a predetermined timing to put the test tube 25 in or take the test tube 25 out of the chamber 45. At the time of image capturing, the lid is closed to prevent external light from entering.

In step ST2, the controller 18 controls the image acquisition portion 14 to perform sidelight image capturing. At the time of sidelight image capturing, the sidelights 42 irradiate the test tube 25 from both sides with light emitted sideways, that is, in the X direction in the present embodiment, with respect to the image capture surface side, to capture the test tube 25 in the upright state from the front side in the Y direction, thereby acquiring image information.

The controller 18 causes the storage 16 to store the image acquired in step ST2 as a first image.

In the sidelight image capturing, light of a preset amount is emitted sideways from the sidelights 42, and light transmitted through the test tube 25 and the specimen 25a is received to perform image capturing. As shown in FIG. 7, the light emitted from the sidelights 42 enters the test tube 25 through the exposed portion 27b, and is reflected at a transparent circumferential wall surface on which the rear surface of the label 27 is attached. In other words, the rear surface of the label 27, namely, an inner curved surface which is not printed, on which an adhesive layer is formed, functions as a reflector. The light reflected at the rear surface of the label 27 transmits through the blood serum. The image capture portion 41 detects the light transmitted through the blood serum and acquires an image.

Figure 8:
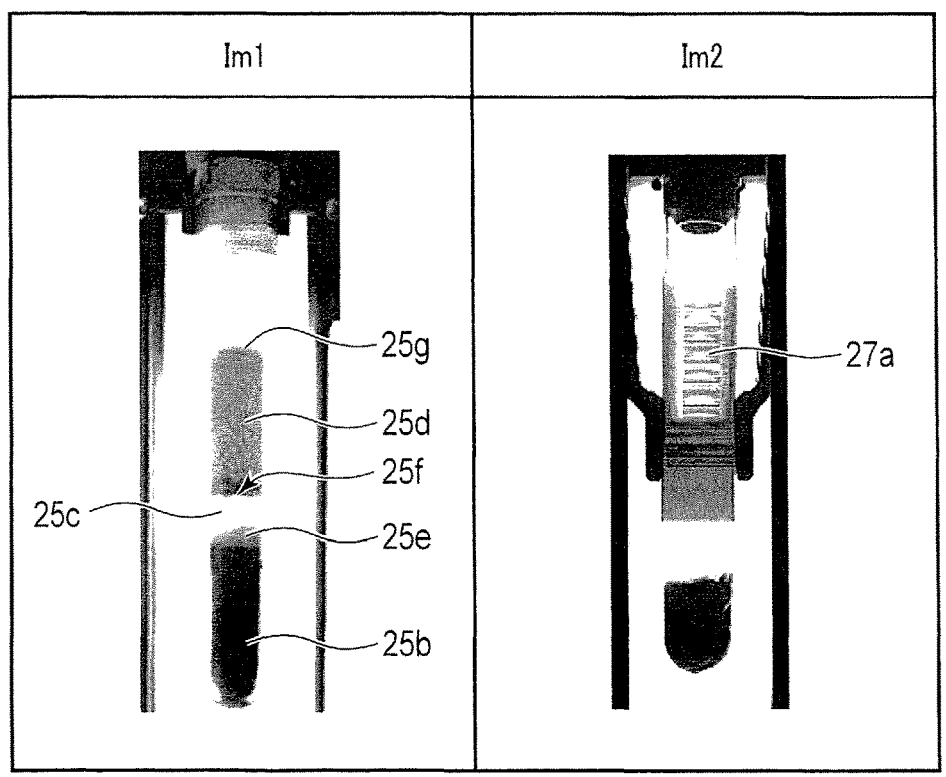
FIG. 8 is an explanatory view showing a sidelight image of a test tube of the specimen information detection apparatus and a backlight image as a comparative example.

In the image acquired by the sidelight image capturing process described above, an influence by the print portion 27a is reduced, since the print portion 27a is not present in a portion where the illumination light transmits, for example as shown in FIG. 7. FIG. 8 shows a first image Im1 acquired through the sidelight image capturing by the pair of sidelights 42, and a backlight image Im2 as a comparative example, acquired through backlight image capturing with light radiating from a back surface side. As shown in FIG. 8, in the backlight image capturing, an image of the label print is captured in the backlight image, since the direction of illumination light coincides with the image capturing direction. In the sidelight image capturing, a capturing of an image of the label print is suppressed and only an image of foreign substances is emphasized, since the direction of illumination light differs from the image capturing direction. Therefore, the sidelight image capturing enables detection of various measurement items with a higher accuracy in comparison with the backlight image capturing.

Figure 9:
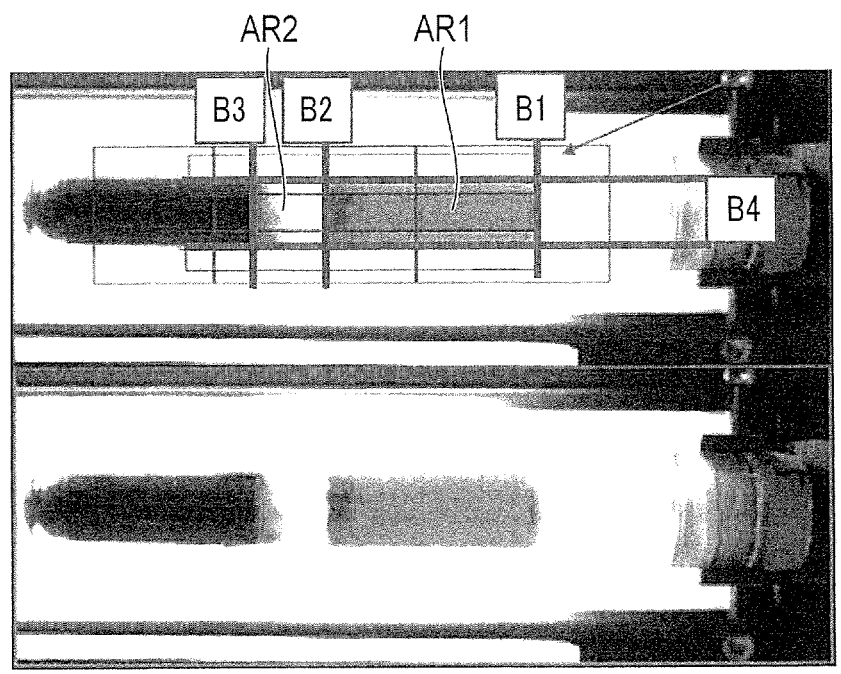
FIG. 9 is an explanatory view showing the specimen information detection method.

Next, the controller 18 performs a boundary position detecting process by image processing based on first image information, and specifies a determination target region AR (step ST3). Specifically, as shown in FIG. 9, the data processor 17 detects a line B1 indicating the specimen liquid surface 25g, a line B3 indicating the first interface 25e, a line B2 indicating the second interface 25f, and a pair of lines B4 indicating the edges of the test tube 25, and detects coordinates as positional information of each line. The controller 18 specifies the determination target region AR based on the obtained various kinds of positional information.

In other words, as shown in FIG. 8 and FIG. 9, a region surrounded by the line B1 of the specimen liquid surface 25g, the line B2 of the second interface 25f, and the lines B4 of the edges of the test tube 25 is specified as a test region AR1 for chyle and hemolysis. A second determination target region AR2 surrounded by the line B1 indicating the specimen liquid surface 25g, the line B2 of the second interface 25f, and the lines B4 of the pair of edges is specified as a target region to determine whether a foreign substance is contained or not.

Next, it is determined whether the specimen contains any substances that are not present in normal blood serum, such as fibrin and defective blood clotting (foreign substances), based on the contrast with surroundings in the determination target region AR2 through image processing (step ST4).

"Fibrin" is the end product of blood coagulation and is a paste-like lump of protein fiber (fibrinogen). In a blood test, red blood cells+fibrin are separated by centrifugation and settled to obtain blood serum as a supernatant. However, if coagulation is delayed more than usual, fibrin precipitation may be incomplete at the time of centrifugation, and precipitation may continue even after separation of the blood serum. In this case, an agar-like semisolid is formed in the blood serum to impede automatic dispensing. Fibrin may have various shapes; some fibrin is visually recognizable, while some is not. Fibrin is a semitransparent substance floating in the blood serum. When fibrin exists, the blood serum in the determination target region has a difference in contrasting density.

"Defective blood clotting" is a state in which the separating medium layer is not formed between the blood serum (blood serum/blood plasma) layer and the blood clot (blood clot/blood cell) layer due to insufficient movement of the separating medium after the centrifugation so that the layers are not completely separated. In this case, automatic dispensing is impeded, as in fibrin precipitation.

In these foreign-substance containing states, contrast is generated between the foreign substance and the surroundings. For this reason, in step ST4, as a foreign-substance containing state determination process, contrast in the determination target region AR2 is detected by an image analysis based on the first image information. Based on the contrast, it is determined that the specimen is in the foreign-substance containing state if the contrast is of a predetermined value or higher.

Furthermore, as step ST5, the data processor 17 performs a hemolysis determination through an image analysis from the first image. "Hemolysis" is a phenomenon wherein red blood cells rupture, and hemoglobin is released from them. At this time, other components of the red blood cells are also released and affect the test values and the like. In this embodiment, the hemolytic state is determined using the characteristic of hemolysis that changes the blood serum color to red.

In the determination of the hemolytic state, the data processor 17 detects color information of the determination target region AR1. For example, a hue value (H) is detected as color information by the HSV method. The data processor 17 determines whether the specimen is in the hemolytic state based on the detected color information.

Furthermore, as step ST6, the data processor 17 determines whether the specimen is in a chylous state. "Chyle" is a state in which a fat has fragmented to make the specimen whitish or the specimen has absorbed a fat and has become whitish. The chyle may make it impossible to accurately measure some blood test items.

In the chylous state, the blood serum layer is whitish and the contrasting density in the blood serum layer is greater than in the normal state. Therefore, as a test-inhibiting object containing state determination process, a contrasting density value (contrasting density information) in the determination target region AR1 is measured through an image analysis based on the first image. If the contrasting density value is a predetermined value or higher, it is determined that the specimen is in the chylous state.

Furthermore, the data processor 17 performs a general final determination based on determination results of various test-inhibiting factor determinations performed in step ST4 to ST6 (step ST7). In the general final determination, for example, based on the result of foreign-substance containing determination, the result of hemolysis predetermination, and the result of chyle determination, if the level of each item is equal to or higher than a predetermined level, the specimen is determined to be untestable. If the level is lower than the predetermined level, the specimen is determined to be testable. If the level falls within a predetermined range, the specimen is determined to be testable, but the test result needs to be corrected.

According to the specimen information detection apparatus 10 of this embodiment, the following effects are obtained.

Since the optical axis of the image capturing and the optical axis of the illumination light are different in direction, the influence of the print portion 27a of the label 27 on image capturing is reduced and the determination can be performed with a high accuracy. Specifically, since the sidelights 42 are disposed on the respective sides of the test tube 25 to make the optical axis of the image capturing and the optical axis of the illumination light different in direction, the light can enter the test tube 25 through the exposed portion 27b and reflect at the rear surface of the label 27, and can enter the image capture portion 41 without transmitting the print portion 27a. For example, in the case of the backlight image capturing, since both the optical axis of the image capturing and the optical axis of the illumination light pass through the print portion, an influence by the print portion is considerable. According to the embodiment described above, since the test tube 25 is irradiated with light emitted sideways, image capturing can be performed with the light transmitting through the exposed portion 27b, without transmitting through the print portion 27a, and being diffracted into the test tube 25. Accordingly, the influence by the print portion of the label 27 is reduced during the image capturing. Thus, by processing and analyzing the sidelight image, the sensing accuracy of the test inhibiting factors of clinical test blood specimens can be improved. In addition, according to the embodiment described above, an image can be used in common to a plurality of types of determination, and a plurality of types of test-inhibiting factors can be determined at a high speed with a high accuracy.

Furthermore, according to the embodiment, the label sensor 32 that detects an edge position of the label 27 is used, and the test tube can be set to an orientation for image capturing by detecting the position of the label 27. Accordingly, the processing efficiency can be further improved.

Second Embodiment

Figure 10:
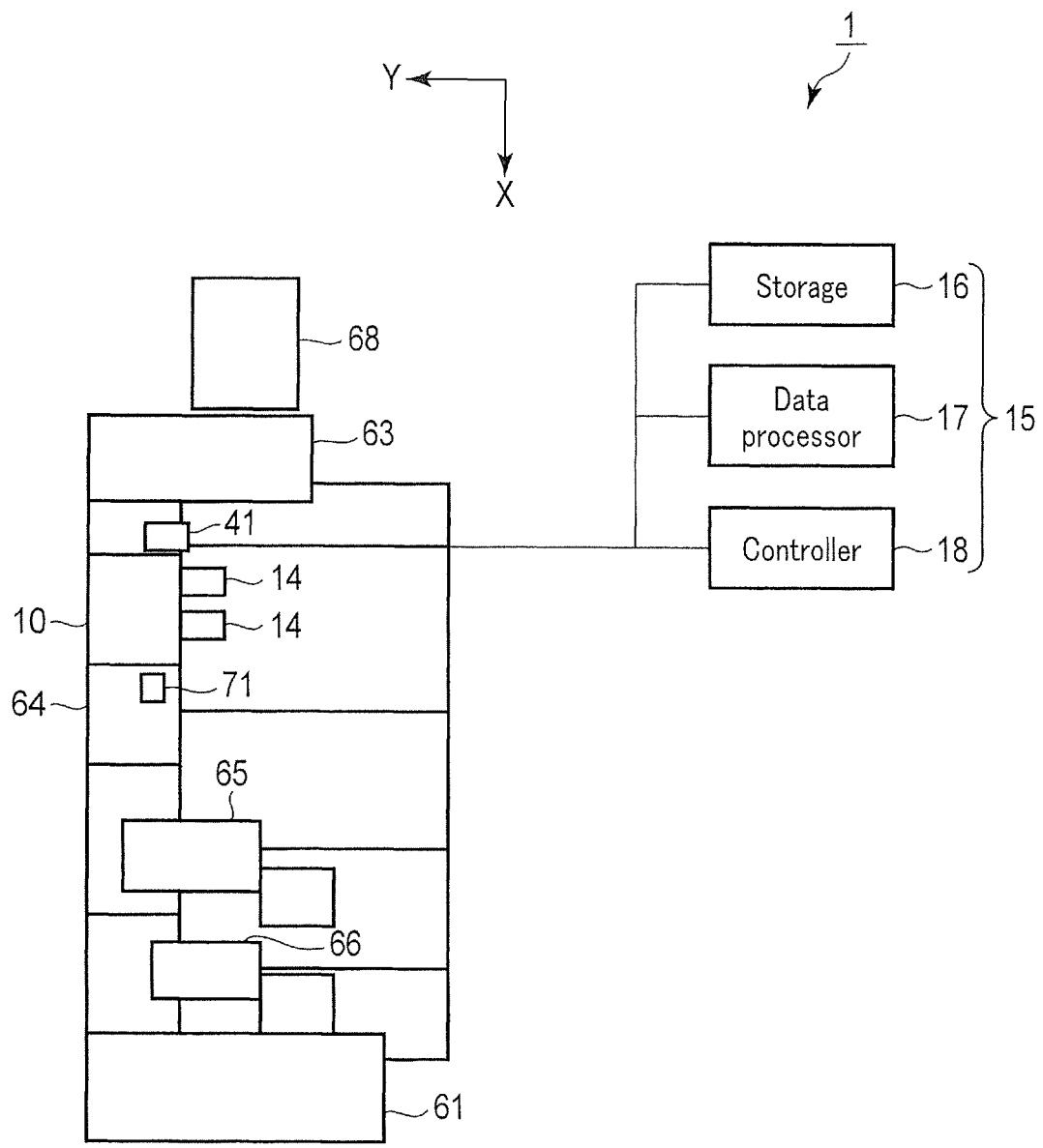
FIG. 10 is an explanatory view of an analysis apparatus according to another embodiment.

As a second embodiment of the present invention, an analysis apparatus 1 serving as a specimen processing apparatus including the specimen information detection apparatus 10 will be described below with reference to FIG. 10. FIG. 10 is a plan view schematically showing the analysis apparatus 1 including the specimen information detection apparatus 10. The analysis apparatus is constituted by juxtaposing a plurality of apparatuses individually constituted so that their conveyance pathways continue.

The analysis apparatus 1 is constructed by arranging a loading device 63, the specimen information detection apparatus 10, a sorting device (sorting means) 64, an unloading device 65, a batch dispensing device (batch dispensing means) 66, and an analysis device 61 in the order of processing from the upstream side to the downstream side of a predetermined conveyance pathway. Each device is provided with a conveyor type conveyance portion that conveys a test tube 25, and the devices are arranged such that the conveyance pathways of the plurality of conveyance portions continue.

The loading device 63 comprises a conveyance portion that conveys a holder 24 along the conveyance pathway, and a transfer mechanism such as a robot arm. The loading device 63 transfers onto the conveyance pathway the test tube 25 from a rack installation portion 68 provided on, for example, a side of the conveyance pathway.

The specimen information detection apparatus 10 is constituted in the same manner as in the first embodiment. The specimen information detection apparatus 10 performs the processing steps of step ST1 to step ST7, in the same manner as in the first embodiment, so as to perform various kinds of test inhibiting factor detection processes through image processing based on image information captured from a side of the test tube 25.

The sorting device 64 comprises a conveyance portion that conveys the holder 24, and a gate portion 71 serving as guide means for guiding the conveyance direction of the holder 24 based on the test inhibiting factor detection result under the control of a controller 18.

A branch portion is provided at the midpoint of the conveyance pathway, and a branch path branching from the conveyance pathway forms a different pathway. The gate portion 71 performs a switching operation to distribute the test tube 25 determined to be untestable to the branch path under the control of the controller 18. For example, the test tube 25 that contains a specimen 25a determined to be untestable due to a test inhibiting factor is guided to the branch path. The normal test tube 25 is guided to be fed to the batch dispensing device 66 on the downstream side along the conveyance pathway. The downstream side of the branch path continues to the unloading device 65 where an additional step is performed for a specimen in the chylous or hemolytic state, namely a step that is not performed for a normal specimen. On the other hand, a normal specimen that is neither in the chylous state nor in the hemolytic state is guided to the batch dispensing device 66 on the downstream side along the conveyance pathway.

The unloading device 65 unloads the test tube 25 that contains the specimen 25a determined to be untestable because of, for example, a test inhibiting factor, and excludes it from the batch dispensing target.

The batch dispensing device 66 comprises a conveyance portion that conveys the holder 24 along the conveyance pathway 20a, and a batch dispensing chip capable of moving up and down and arranged to face the opening of the test tube 25. When the test tube 25 with the specimen is arranged and stopped at a predetermined position on the conveyance pathway, the batch dispensing chip measures off a predetermined amount of blood serum from the test tube 25 containing the specimen and dispenses the measured blood serum into a sample cup that is separately fed. The sample cup in which the blood serum has been dispensed is loaded into the analysis device 61 on the downstream side so as to undergo an analysis process.

Figure 11:
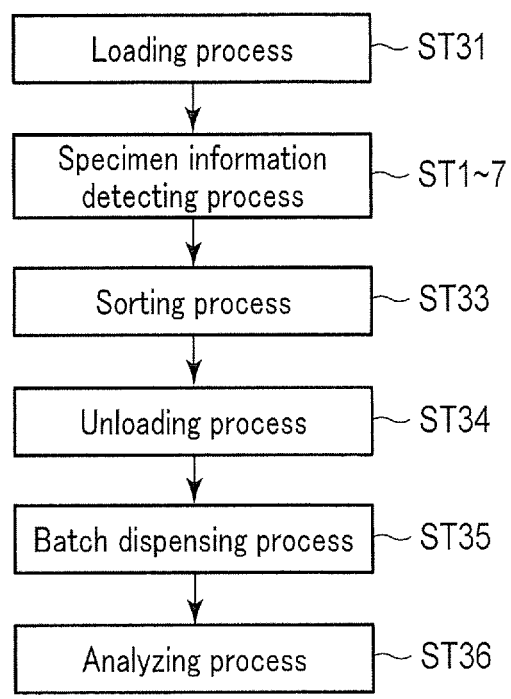
FIG. 11 is a process explanatory view showing processing steps of the analysis apparatus.

The processing procedure of the analysis apparatus 1 will be described next with reference to FIG. 11. FIG. 11 shows a flow of processing of the analysis apparatus 1. First, a loading process is performed by the loading device 63 provided on the upstream side to grip the test tube 25 containing the specimen stored in a test tube rack on the rack installation portion 68 and transfer it onto the conveyance pathway (step ST31). The holder 24 stands by on the conveyance pathway. The test tube 25 is set in the holder 24. The transferred test tube 25 is fed along the conveyance pathway to the specimen information detection apparatus 10 in the state of being held in the holder 24.

The specimen information detection apparatus 10 performs the processing of steps ST1 to ST7 in the same manner as in the first embodiment. The test tube 25 that has undergone the test inhibiting factor detection processes is fed to the sorting device 64 on the downstream side while being held in the upright state in the holder 24.

The sorting device 64 provided on the downstream side of the specimen information detection apparatus 10 switches the gate portion 71 in accordance with the general determination result in step ST7 so as to distribute the test tube 25 under the control of the controller 18 (step ST33). For example, the test tube 25 containing the specimen 25a determined to be untestable is guided to the branch path and is thus guided to the unloading device 65 on the downstream side by switching of the gate portion 71. On the other hand, a normal specimen that is neither in the chylous state nor in the hemolytic state is guided to the batch dispensing device 66 on the downstream side along the conveyance pathway.

The unloading device 65 on the downstream side of the branch path unloads the test tube 25 that contains the specimen 25a determined to be untestable because of a test inhibiting factor, and excludes it from the batch dispensing target (step ST34).

In the batch dispensing device 66, a batch dispensing process is performed by the batch dispensing chip that measures off a predetermined amount of blood serum from the test tube 25 containing the normal specimen and dispenses it into a sample cup that is separately fed (step ST35). The sample cup in which the blood serum has been dispensed is unloaded from the unloading device on the downstream side and loaded into the analysis device 61 via a downstream connection path. The analysis device 61 performs an analyzing process of testing various kinds of reactions (step ST36).

According to the analysis apparatus 1 of this embodiment, a test inhibiting factor is detected in advance by test preprocessing, thereby changing the reagent dilution ratio or test conditions in accordance with the test inhibiting factor before an analysis process or excluding the specimen from the test target. This can prevent waste of test processes or reagents. In addition, when an image analysis is performed using an image common to a plurality of test inhibiting factors, detection can be performed at a high speed with a high accuracy. In addition, according to the embodiment described above, an image can be used in common to a plurality of types of determination, and a plurality of types of test inhibiting factors can be determined at a high speed with a high accuracy.

The present invention is not limited to the above-described embodiments and can be embodied in practice by modifying the structural elements without departing from the gist of each invention. For example, a case has been described for the above embodiments in which specimen processing is performed for each test tube 25. However, the processing may be performed simultaneously for a plurality of test tubes 25.

In the above embodiments, a case has been described in which a plurality of test inhibiting factors including the states of containing a foreign substance, such as fibrin and defective blood clotting as well as chyle and hemolysis, are detected. Some items may be omitted, and other items may be added. For example, an icterus state may be further detected as a test inhibiting factor. "Icterus" is a state in which the amount of bilirubin in blood increases, and the tissues of skin, mucosae, and the like are stained yellow. In blood serum, the yellowness tends to deepen due to the increase in the bilirubin amount. Therefore, the icteric state can be detected by, for example, the RGB method.

The method for detecting chyle, hemolysis, and foreign-substance containing states by analyzing the first image is not limited to the above, and various image analyses are applicable to the method. For example, an example is described in which hemolysis is determined on the basis of a hue value (H) as color information. However, the embodiments are not limited thereto. For example, a color component of red (R) in the determination target region may be extracted by the RGB method through image processing. Based on the value of the red component, if the value of the R component is a predetermined value or higher, it may be determined that the specimen is in the hemolysis state.

The example is described in which judgments about chyle are made on the basis of a contrasting density value. However, the embodiments are not limited thereto. For example, it may be determined that the chylous state exists based on a light transmittance. As a specific example of a light transmittance index, a value of V (luminance) of a hue circle in the HSV method may be used. Alternatively, the shutter speed of the camera of the image capture portion 41 may be adjusted, and the transmittance corresponding to the shutter speed at which a predetermined luminance can be obtained may be used as a light transmittance index.

The embodiments described above are targeted to the test tube 25 that includes the exposed portion 27b formed in advance in a predetermined region. However, the embodiments are not limited thereto. For example, a label peeling device for peeling off the label 27 of the test tube 25 before image acquisition may be provided on the upstream side of the conveyance pathway or may be provided as a separate device so as to peel off a predetermined region necessary for image capture as preprocessing of image capture even if the exposed portion 27b is not formed at a predetermined position.

In the embodiments described above, the label sensor 32 and the rotation device 33 are disposed on the upstream side of the transfer device 19. However, the embodiments are not limited thereto. Furthermore, an example is described in which the process for adjusting the orientation of the label is performed before the test tube is transferred. However, the embodiments are not limited thereto. For example, the label sensor 32 that detects a position of an edge of the label 27 or the rotation device 33 that rotates the test tube 25 may be disposed inside the chamber 45 as a part of the image acquisition portion 14. In this case, after the test tube 25 is transferred into the chamber 45 by the transfer device 19, the position detection of the label 27 or the adjustment of the orientation of the test tube 25 may be performed by the rotation device 33 and the label sensor 32.

Each structural element exemplified in the above embodiments may be omitted, and the shape, structure, and material, and the like of each structural element may be changed. Various inventions can be made by properly combining a plurality of structural elements disclosed in the above embodiments.

The invention claimed is:

1. A specimen information detection apparatus comprising:
   an image capture device comprising a camera and configured to capture an image of a specimen container that contains a specimen, wherein the specimen container comprises a label including a print portion indicating a barcode and an exposed portion in at least a part of an outer circumferential surface where no label is attached;
   an illumination device comprising a light and configured to irradiate the specimen container with light sideways with respect to an image capturing direction when the image is captured, wherein the illumination device is configured to irradiate the specimen container with light emitted from both sides in a light irradiation direction intersecting the image capturing direction in which the specimen container aligns with an image detection axis when the image is captured;

wherein the illumination device is disposed so that a center angle between the light irradiation direction and the image capturing direction at a center position of the specimen container is in a range of 60 degrees to smaller than 90 degrees and in such a positional relationship that the light emitted from the illumination device can enter the specimen container through the exposed portion and reflect at a rear surface of the label, functioning as a reflector, to the image capture device without transmitting through the print portion of the label; and a hardware processor configured to detect a chylous state, a hemolysis state, or a foreign substance containing state in the specimen container through image processing based on image information of the specimen container acquired by capturing the image of the specimen container; and wherein the specimen information detection apparatus further comprises:

a chamber configured to house the specimen container and block an external light when the image is captured;

a label sensor configured to detect a position of an edge of the label of the specimen container, thereby detecting an orientation of the specimen container; and a rotation device comprising a roller and configured to adjust the orientation of the label attached to the outer circumferential surface of the specimen container before the image is captured, such that the print portion indicating said barcode faces an opposite side of the image capture device as viewed in the image capturing direction.

2. The specimen information detection apparatus according to claim 1, wherein the hardware processor is configured to:

detect contrasting density information of an image in a target region through image processing from image information of the specimen container acquired by capturing an image of the specimen container prior to a test process of the specimen to detect a chylous state of the specimen based on the contrasting density information; and detect color information of the specimen through image processing from the image information to detect a hemolysis state of the specimen based on the color information.

3. The specimen information detection apparatus according to claim 1, wherein the hardware processor is configured to detect a contrast in a target region from the image information through image processing to detect a foreign-substance containing state of the specimen based on the contrast.

4. A specimen information detection method comprising:

capturing with a camera an image of a specimen container that contains a specimen, wherein the specimen container comprises a label including a print portion indicating a barcode and an exposed portion in at least a part of an outer circumferential surface where no label is attached;

irradiating the specimen container with a light sideways with respect to an image capturing direction when the image is captured, wherein the light is emitted from both sides in a light irradiation direction intersecting the image capturing direction in which the specimen container aligns with an image detection axis when the image is captured;

wherein the light is disposed so that a center angle between the light irradiation direction and the image capturing direction at a center position of the specimen container is in a range of 60 degrees to smaller than 90 degrees and in such a positional relationship that the light emitted from the light enters the specimen container through the exposed portion and reflect at a rear surface of the label, functioning as a reflector, to the camera without transmitting through the print portion of the label; and detecting a chylous state, a hemolysis state, or a foreign-substance state in the specimen container through image processing based on image information of the specimen container acquired by capturing the image of the specimen container; and wherein the specimen information detection method further comprises:

detecting a position of an edge of the label of the specimen container by a label sensor, thereby detecting an orientation of the specimen container; and adjusting an orientation of the label attached to the outer circumferential surface of the specimen container before the image is captured, such that the print portion indicating said barcode faces an opposite side of the camera as viewed in the image capturing direction.

5. The specimen information detection method according to claim 4, comprising:

detecting contrasting density information of an image in a target region through image processing from image information of the specimen container acquired by capturing an image of the specimen container prior to a test process of the specimen to detect a chylous state of the specimen based on the contrasting density information; and detecting color information of the specimen through image processing from the image information to detect a hemolysis state of the specimen based on the color information.

6. The specimen information detection method according to claim 4, comprising: detecting a contrast in a target region from the image information through image processing to detect a foreign-substance containing state of the specimen based on the contrast.

7. The specimen information detection apparatus according to claim 2, wherein the hardware processor is configured to detect a contrast in a target region from the image information through image processing to detect a foreign-substance containing state of the specimen based on the contrast.

* * * * *